United States Patent [19]

Worschech et al.

[11] Patent Number: 4,767,575

[45] Date of Patent: Aug. 30, 1988

[54] MELT-PHASE SYNTHESIS OF DIBASIC ORGANO-LEAD COMPOUNDS

[75] Inventors: Kurt Worschech; Peter Wedl, both of Loxstedt; Erwin Fleischer, Bremerhaven-Spaden; Frido Loeffelholz, Bremerhaven-Surheide, all of Fed. Rep. of Germany

[73] Assignee: Neynaber Chemie GmbH, Loxstedt, Fed. Rep. of Germany

[21] Appl. No.: 806,247

[22] Filed: Dec. 5, 1985

[30] Foreign Application Priority Data

Dec. 5, 1984 [DE] Fed. Rep. of Germany ....... 3444261

[51] Int. Cl.⁴ ........................... C07F 7/24; C11C 1/00
[52] U.S. Cl. ..................................... 260/414; 556/82; 556/105
[58] Field of Search ................... 556/82, 105; 260/414

[56] References Cited

U.S. PATENT DOCUMENTS

| | | | |
|---|---|---|---|
| 1,729,823 | 10/1929 | Dimmig | 260/414 X |
| 1,830,984 | 11/1931 | Diggs et al. | 260/414 X |
| 3,002,943 | 10/1961 | Kebrich | 556/105 X |
| 3,461,081 | 8/1969 | Sugahara et al. | 252/400 |
| 3,519,571 | 7/1970 | Szczepanek et al. | 260/414 X |
| 3,546,263 | 12/1970 | Ruf | 556/105 X |
| 3,562,180 | 2/1971 | White et al. | 556/105 X |
| 3,639,264 | 2/1972 | Roussos et al. | 556/105 X |
| 3,803,188 | 4/1974 | Scott et al. | 260/414 X |
| 4,316,852 | 2/1982 | Blachford | 556/105 X |
| 4,324,768 | 4/1982 | Sugahara et al. | 556/105 X |
| 4,421,886 | 12/1983 | Worschech et al. | 524/310 |

FOREIGN PATENT DOCUMENTS

| | | |
|---|---|---|
| 1768450 | 3/1972 | Fed. Rep. of Germany . |
| 2652328 | 5/1978 | Fed. Rep. of Germany . |
| 684155 | 12/1952 | United Kingdom . |
| 1136935 | 12/1968 | United Kingdom . |
| 1173814 | 12/1969 | United Kingdom . |

OTHER PUBLICATIONS

European Search Report (copy).

Primary Examiner—Paul F. Shaver
Attorney, Agent, or Firm—Ernest G. Szoke; Henry E. Millson, Jr.; Mark A. Greenfield

[57] ABSTRACT

Dibasic lead-fatty acid salts are synthesized in a melt reaction between plumbous oxide and fatty acids in the presence of magnesium, calcium, and/or aluminum compounds. The salts are useful as stabilizers for halogen-containing polymers.

26 Claims, No Drawings

MELT-PHASE SYNTHESIS OF DIBASIC ORGANO-LEAD COMPOUNDS

BACKGROUND OF THE INVENTION

1. Field of the Invention

The melt-reaction synthesis of dibasic plumbousfatty acid salts and their use as stabilizers in the production of rigid halogen-containing polymers.

2. Statement of the Related Art

Stabilizers based on lead compounds are widely used in the production of moldings of halogen-containing polymers, particularly rigid polyvinyl chloride. Stabilizer systems of this type are not only highly effective, they are also inexpensive. In addition, they provide the plastic end products with effective light stabilization. For many years, formulations containing stabilizers based on lead compounds have normally contained primary stabilizers, (also known as pigment stabilizers) because of their covering power. These stabilizers are generally basic lead sulfates.

Other suitable stabilizers are organic lead salts, particularly lead fatty acid soaps. Of particular importance are the commercial lead stearates which are used either as dibasic lead stearate, 2 PbO.Pb(fatty acid residue)$_2$ - 51% by weight lead stearate, or as neutral lead stearate Pb(fatty acid residue)$_2$ - 28% by weight lead stearate. In many cases, combinations of these two are also used.

The stabilizer system is generally completed by calcium soaps, particularly commercial calcium stearate. These metal soaps may also be counted as part of the lubricant system which normally contains paraffins, optionally free fatty acids, other hydrocarbon waxes such as polyethylene derivatives, and, in some cases, fatty acid esters.

In recent years, the economic need to find less expensive formulations has resulted in the growing elimination of pigment stabilizers of the basic lead sulfate type. In addition, developments in the field of processing machines for plastics have meant that molding compositions based on halogen-containing polymers containing far less stabilizer can now be extruded without difficulty. Accordingly, the basic lead soaps 2PbO.Pb(fatty acid residue)$_2$ primarily stearates, are increasingly becoming the focus of interest as primary stabilizers. Neutral lead soaps (stearates) optionally together with calcium soaps (stearates) are being used as rheologically active constituents of the formulation and as co-stabilizers. By contrast, there has been little change in the other components of the stabilizers/lubricant systems still used for halogen-containing polymers.

Mixtures of the type in question here offer the incentive to produce the entire stabilization and rheology system in the form of a melt compound. Proposals to that effect can be found, for example, in U.S. Pat. No. 3,461,081 and U.K. patent No. 1,136,935, as well as their corresponding German patent Nos. 1,544,697 and 1,569,190. These publications describe non-dusting stabilizer/lubricant combinations for vinyl chloride polymers which comprise a mixture—combined in the melt—of lubricants, metal soaps of a long-chain aliphatic carboxylic acid and basic lead salts of inorganic or organic acids. However, experience has shown that it is difficult, if not impossible, to produce dibasic lead soaps (stearates) and, in particular, defined quantities of dibasic lead soaps in addition to neutral lead soaps (stearates), by the melt process. Accordingly, it is proposed in the above publications to introduce separately prepared dibasic lead soaps into the melt of lubricants and/or neutral lead soaps.

DESCRIPTION OF THE INVENTION

The present invention affords a simple process by which dibasic lead fatty acid salts can be produced in situ by the melt process. More particularly, the invention seeks to provide a melt process in which predetermined quantitative ratios of neutral lead soaps to dibasic lead soaps of the type mentioned can be established by the melt process. Through the new process, the invention seeks to provide a simple way of melt phase producing stabilizer systems for halogenated polymers, more especially polyvinyl chloride, which combines mixing of the constituents with the production of essential components in the melt.

The accomplishment of this invention is based on the surprising discovery that basic lead soaps can be produced in the melt from neutral lead soaps providing certain mixture components are present in the melt.

Accordingly, the present invention relates to a process for the production of plumbous lead-fatty acid salts by reaction of plumbous oxide with a melt of those fatty acids which form lead salts, especially in the production of stabilizer mixtures for halogenated polymers, particularly polyvinyl chloride. It is characterized in that a melt containing at least one magnesium, calcium or aluminum catalyst compound compatible with halogenated polymers is used in the production of dibasic lead salts corresponding to the formula 2PbO.Pb(fatty acid residue)$_2$.

In the process according to the invention, the dibasic lead salt is formed in a melt of the neutral lead fatty acid salt or in melts containing the neutral lead fatty acid salt. Finely divided plumbous oxide is introduced into these melts. The introduction of plumbous oxide is effected by changing the plumbous oxide to a melt of the fatty acid capable of forming a lead-fatty acid salt, and admixing the catalyst/initiator, said changing and admixing being in any order and repeatable. The lead oxide is quickly reacted in the presence of the magnesium, calcium and/or aluminum initiator compounds mentioned, as clearly reflected in the disappearance of the yellow oxide color. In the absence of the foregoing catalysts, there is no reaction with the introduced lead oxide, which would remain in the melt in the form of yellow particles partly suspended and partly sedimentary.

Examples of specific catalysts include: magnesium hydroxide, magnesium oxide, magnesium carbonate, calcium hydroxide, calcium oxide, calcium carbonate and aluminum hydroxide, preferably in their respective anhydrous forms.

In one particularly important embodiment of the invention, the melts in which the dibasic plumbous fatty acid salts are produced contain at least one magnesium, calcium, or aluminum soap. Particular importance is attributed to these soaps by virtue of their stabilizing and lubricating properties when used in stabilizer mixtures for halogen-containing polymers. Preferred soaps are the magnesium, calcium and/or aluminium salts of $C_{12-24}$, preferably $C_{16-18}$, fatty acids, which may be linear or branched. In general, the fatty acid component of these soaps consists of the fatty acids occurring in natural fats and oils, such as lauric, myristic, palmitic and stearic acid. The soaps mentioned may be salts of individual fatty acids, or of a mixture of various fatty acids with carbon chain lengths in the above-mentioned ranges. Mixtures of palmitic acid and stearic acid, i.e. $C_{16-18}$ fatty acids, are particularly important. The magnesium, calcium and aluminum soaps mentioned may be introduced as such into the melt used for formation of the dibasic lead salts. Normally, it is preferred to form the soaps in situ in the melt used for formation of the dibasic lead salts. In that case, the fatty acid component of the magnesium, calcium and/or aluminum soaps is obtained from the lead-salt-forming fatty acid and the soaps are produced in the melt by dissolving a corresponding quantity of magnesium hydroxide, magnesium oxide, calcium hydroxide, calcium oxide or aluminum hydroxide before the lead oxide required for formation of the dibasic lead salt from the neutral lead salt is added.

It should be noted that the oxides and hydroxides of magnesium and calcium and aluminum hydroxide also appear to catalyze formation of the dibasic lead salt in the sense of the invention even when they are not converted into the corresponding soaps. This effect also occurs when the compounds mentioned are only introduced into the melt after all the fatty acid present has reacted with lead oxide to form the neutral lead soap.

The metal compounds mentioned above need only be used in very small quantities to initiate and promote the hitherto inaccessible melt-phase reaction of plumbous oxide with the neutral lead soap to form the dibasic lead soap. The catalytic quantities may even be sufficient. It is preferred to use melts which contain at least 5% by weight, most preferably 5 to 10% by weight, based on the total lead salt in the end product, of magnesium, calcium and/or aluminum compound. The upper limit to the content of the above-mentioned compounds in the melts is not critical to the inventive process. The oxides and hydroxides of magnesium, calcium and aluminum do not have any particular effects on the halogenated polymers themselves. However, the magnesium, calcium and aluminum soaps are compounds which may be required in the system as stabilizer and/or lubricant components. In this connection, the soaps mentioned may make up as much as 25% by weight of the end product, based on the total lead salt present therein. These soaps may be present in the melt ab initio in the total amount necessary or may be added in partial amounts during the melt-phase formation of the dibasic lead soaps.

It is possible, using the process of this invention, to produce mixtures of neutral and dibasic lead salts in which the dibasic lead salts make up as much as 50% by weight of the lead salts present. The fatty acid component of the lead salts and, of course, the fatty acid starting material, comprise linear and/or branched $C_{12-24}$ fatty acids, which preferably are saturated. In general, the fatty acid component of the lead salts comprise fatty acids occurring in natural fats and oils, for example lauric, myristic, palmitic and stearic acid. These acids may be present as individual chemicals, or more commonly as a mixture of different fatty acids having C-chain lengths in the above-mentioned range. In this connection, particular importance is attributed to mixtures of $C_{16-18}$ fatty acids, i.e. palmitic and stearic acid, mixtures in which the two acids are present in approximately equal parts by weight being of special significance.

In the most simple case, defined mixtures of neutral and dibasic lead fatty acid salts are produced by adding plumbous oxide to melts of neutral plumbous fatty acid salts containing at least one of the magnesium, calcium and/or aluminum compounds mentioned. In addition to the neutral plumbous fatty acid salts, these melts may contain fusible components desired in stabilizer/lubricant combinations which are inert to the lead oxide added. Examples of these include: those paraffins known for their lubricant properties; neutral fatty acid esters of mono- and poly-alcohols; polycarboxylic acid fatty alcohol esters; and complex esters of polyalcohols, dicarboxylic acids, fatty acids, polyalcohols, polycarboxylic acids, or fatty alcohols.

In one preferred embodiment of the process according to the invention, the neutral lead salt is initially formed by the reaction of plumbous oxide with the fatty acid in the melt. The intended magnesium, calcium and/or aluminum compound is then added to the melt. If it is intended to add magnesium, calcium or aluminum soaps to the melt, these soaps are produced in the melt as above-described. More plumbous oxide is then introduced into the melt in such quantities that, on completion of the reaction with the lead oxide added in the second stage, the reaction mixture contains neutral and dibasic lead salt in a predetermined ratio. In preferred embodiments of the invention, predetermined ratios by weight of neutral lead soaps to dibasic lead sopas of 1:0.05–1, most preferably 1:0.5–1, may generally be obtained.

If desired, the melt-phase reaction according to the invention may be carried out in the presence of other inert components dissolved and/or suspended in the melt, of the type normally used in particular in stabilizer/lubricant systems for halogen-containing polymers, more especially polyvinyl chloride. It is also possible within the scope of the invention to add the components desired for the intended application to the melt systems accumulating as reaction products. Non-dusting stabilizer/lubricant combinations are obtained in this way and may be converted into granulates or any other finely divided forms by known methods.

The process according to the invention has the important advantages, that the melt soaps can be produced without harm to the environment and that stabilizer systems can be produced in virtually a single step from a lead compounds, namely plumbous oxide. In use, the mixtures of neutral and dibasic lead soaps produced by the melt process behave similarly to corresponding mixtures of precipitated soaps. In particular, melt soap granulates produced in accordance with the invention may readily be worked up with halogenated polymers into dry blends in a known manner, for example in fluid mixers. The dry blends thus prepared may then be subjected to molding, for example in twinscrew extruders for the production of PVC pipes. The residual stability of the molded material is sufficient even to guarantee the reprocessing of starting material.

EXAMPLES

EXAMPLE 1

In an open glass vessel equipped with a stirrer and thermometer, 102.0 g (0.38 mol) of a technical $C_{16-18}$ fatty acid (MW 270) and 27.0 g of paraffin (Mp. 75°–80° C.) were melted and heated to 150° C. 38.3 g (0.17 mol) of plumbous oxide (litharge) were then introduced into the melt with stirring over a period of 2 minutes during which the reaction temperature was kept at 150°–160° C. After stirring for another 2 minutes, a clear yellowish melt was formed. 1.3 g (0.02 mol) of calcium hydroxide and 5 g of bisphenol A were then added to the melt. Thereafter, 30 g (0.13 mol) of litharge were introduced into the melt which was kept at 150°-160° C. over a period of 8 minutes. The melt was then stirred for another 30 minutes at 150°-160° C. By this time, the lead oxide added had dissolved and the reaction mixture was in the form of a clouded yellowish melt tinged with gray and without any sediment which, on cooling, solidified to a beige-colored solid resembling a hard wax (Mp. 102° C.).

EXAMPLE 2

As in Example 1, 56.6 g (0.21 mol) of a technical $C_{16-18}$ fatty acid (MW 270) and 49.5 g of hard paraffin (Mp. 100° C.) were melted by heating to 150° C. to form a clear, yellow-tinged liquid. 23.4 g (0.105 mol) of litharge were then introduced into the melt with stirring over a period of 2 minutes at 150°-155° C. After stirring for another 2 minutes, a clear yellow melt was formed. Thereafter, 4.5 g of calcium carbonate and then 18.0 g (0.08 mol) of litharge were introduced into the melt. The mixture was then stirred for another 30 minutes at 150°-160° C. By this time, the lead oxide added had dissolved. The reaction mixture was a clouded yellowish melt tinged with brown and without any sediment which, on cooling, solidified to a faintly caramel-colored wax-like solid (Mp. 100° C.).

EXAMPLE 3

As in Example 1, 92.8 g (0.34 mol) of a technical $C_{16-18}$ fatty acid (MW 270) and 37.0 g of paraffin (Mp. 75°-80° C.) were heated to 150° C. 38.0 g (0.17 mol) of litharge were introduced into the melt over a period of 3 minutes. After stirring for another 5 minutes, a clear yellowish melt was formed. Thereafter, 10 g of magnesium stearate and 5 g of bisphenol A were stirred into the melt before 30.0 g (0.13 mol) of litharge were added over a period of 3 minutes. The mixture was then stirred for another 30 minutes at 150°-160° C. By this time, the yellow color of the added plumbous oxide had disappeared. The reaction mixture was a yellow melt tinged with brown without an any sediment which, on cooling, solidified to a yellowish wax-like solid tinged with brown.

EXAMPLE 4

As in Example 1, 92.8 g (0.34 mol) of a technical $C_{16-18}$ fatty acid (MW 270) and 27 g of paraffin (Mp. 75°-80° C.) were melted and heated to 150° C. 38.0 g (0.17 mol) of litharge were stirred into the melt over a period of 3 minutes, followed by stirring for another 5 minutes. 16 g of aluminum stearate and 5 g of bisphenol A were then successively added to the clear yellowish melt formed. Thereafter, 30.0 g (0.13 mol) of litharge were added over a period of 3 minutes and the mixture stirred for 60 minutes at 150°-160° C. By this time, the added plumbous oxide had dissolved. The reaction mixture was a brownish-yellow melt which, on cooling, solidified to a brown-tinged wax-like solid.

We claim:

1. A method for the synthesis of dibasic lead-fatty acid salts of the formula 2PbO.Pb (fatty acid residue)$_2$ in a melt reaction comprising:
    melting at least one fatty acid capable of forming a lead-fatty acid salt;
    charging thereto plumbous oxide in an amount effective to form a given amount of said dibasic lead-fatty acid salt; and
    admixing a catalyst/initiator consisting essentially of at least one magnesium, calcium or aluminum compound in an amount of at least sufficient to effectuate said synthesis; said charging and admixing being in any order and repeatable.

2. The method of claim 1 wherein said at least one fatty acid has 12 to 24 carbon atoms.

3. The method of claim 1 wherein said fatty acid consists essentially of at least one of lauric, myristic, palmitic, or stearic.

4. The method of claim 1 wherein said fatty acid consists essentially of a mixture of palmitic and stearic acids in approximately equal parts by weight.

5. The method of claim 1 wherein said catalyst/initiator consists essentially of at least one of magnesium hydroxide, magnesium oxide, magnesium carbonate, calcium hydroxide, calcium oxide, calcium carbonate, or aluminum hydroxide.

6. The method of claim 3 wherein said catalyst/initiator consists essentially of at least one of magnesium hydroxide, magnesium oxide, magnesium carbonate, calcium hydroxide, calcium oxide, calcium carbonate, or aluminum hydroxide.

7. The method of claim 4 wherein said catalyst/initiator consists essentially of at least one of magnesium hydroxide, magnesium oxide, magnesium carbonate, calcium hydroxide, calcium oxide, calcium carbonate, or aluminum hydroxide.

8. The method of claim 1 wherein said catalyst/initiator consists essentially of at least one magnesium soap, calcium soap, or aluminum soap.

9. The method of claim 1 wherein said catalyst/initiator consists essentially of at least one magnesium, calcium or aluminum, $C_{12-24}$-fatty acid soap.

10. The method of claim 3 wherein said catalyst/initiator consists essentially of at least one magnesium, calcium or aluminum, $C_{12-24}$-fatty acid soap.

11. The method of claim 1 wherein said catalyst/initiator consists essentially of at least one magnesium, calcium, or aluminum, $C_{16-18}$-fatty acid soap.

12. The method of claim 4 wherein said catalyst/initiator consists essentially of at least one magnesium, calcium, or aluminum, $C_{16-18}$-fatty acid soap.

13. The method of claim 1 wherein said catalyst/initiator is employed in an amount of at least 5% by weight, based upon the total weight of lead salt in the synthesis end product.

14. The method of claim 1 wherein said catalyst/initiator is employed in an amount of about 5-10% by weight, based upon the total weight of lead salt in the synthesis end product.

15. The method of claim 10 wherein said catalyst/initiator is employed in an amount of about 5-10% by weight, based upon the total weight of lead salt in the synthesis end product.

16. The method of claim 12 wherein said catalyst/initiator is employed in an amount of about 5-10% by weight, based upon the total weight of lead salt in the synthesis end product.

17. The method of claim 1 wherein said admixing is effected prior to said charging.

18. The method of claim 8 wherein said soap is itself formed within the reaction melt by first adding thereto at least one of: magnesium hydroxide, oxide, or carbonate; calcium hydroxide, oxide, or carbonate; or aluminum hydroxide; and wherein said admixing is effected prior to said charging.

19. The method of claim 1 wherein a mixture of neutral lead-fatty acid salt and dibasic lead-fatty acid salt in a predetermined ratio is obtained by sequentially:
- forming substantially neutral lead-fatty acid salt by charging said plumbous oxide;
- admixing said at least one magnesium, calcium, or aluminum compound; and
- charging additional said plumbous oxide to convert said neutral lead-fatty acid salt to dibasic lead-fatty acid salt in an amount determined by the additional amount of said plumbous oxide.

20. The method of claim 19 wherein said predetermined ratio of neutral to dibasic lead-fatty acid salt is about 1:0.05–1 by weight.

21. The method of claim 19 wherein said predetermined ratio of neutral to dibasic lead-fatty acid salt is about 1:0.5–1 by weight.

22. The method of claim 1 wherein inert components, not reactive in said synthesis, are present in the reaction melt.

23. A mixture of magnesium, calcium, or aluminum-fatty acid salts and neutral and dibasic lead-fatty acid salts, synthesized by the method of claim 1.

24. A mixture of magnesium, calcium, or aluminum-fatty acid salts and neutral and dibasic lead-fatty acid salts, synthesized by the method of claim 19.

25. A mixture of magnesium, calcium, or aluminum-fatty acid salts and dibasic lead-fatty acid salts, synthesized by the method of claim 21.

26. A mixture of magnesium, calcium, or aluminum-fatty acid salts, neutral and dibasic lead-fatty acid salts, and inert components not reactive in the synthesis, synthesized by the method of claim 22.

* * * * *